(12) United States Patent
Jih

(10) Patent No.: US 9,370,597 B2
(45) Date of Patent: Jun. 21, 2016

(54) AIR PURIFIER

(71) Applicant: PRIOR COMPANY LIMITED, Taipei (TW)

(72) Inventor: Eric Jih, New Taipei (TW)

(73) Assignee: Prior Company Limited, Taipei (TW)

( * ) Notice: Subject to any disclaimer, the term of this patent is extended or adjusted under 35 U.S.C. 154(b) by 150 days.

(21) Appl. No.: 14/514,942

(22) Filed: Oct. 15, 2014

(65) Prior Publication Data

US 2016/0106876 A1    Apr. 21, 2016

(51) Int. Cl.
| | |
|---|---|
| *B01D 47/02* | (2006.01) |
| *B01F 3/04* | (2006.01) |
| *A61L 9/12* | (2006.01) |
| *A61L 9/14* | (2006.01) |

(52) U.S. Cl.
CPC . *A61L 9/122* (2013.01); *A61L 9/14* (2013.01); *B01D 47/021* (2013.01); *B01D 47/024* (2013.01); *B01F 3/04106* (2013.01)

(58) Field of Classification Search
CPC .... B01D 47/02; B01D 47/021; B01D 47/024; B01F 3/04; B01F 3/04106; B01F 3/04099
USPC .......... 261/30, DIG. 88; 96/329, 332
See application file for complete search history.

(56) References Cited

FOREIGN PATENT DOCUMENTS

WO    WO 2005051519 A1 * 6/2005 ............. A61L 9/122

* cited by examiner

*Primary Examiner* — Robert A Hopkins
(74) *Attorney, Agent, or Firm* — Rosenberg, Klein & Lee

(57) ABSTRACT

An air purifier has a lower base, an upper cover, and a middle sector in between to accommodate a blast component, a light-emitting element, a control unit, and a power supply base. The middle sector has an air intake, a passage, and an air outlet hidden inside the upper cover. The upper space of the upper cover has a fluid communication with the exterior via the air intake and a lower annular gap between the lower base and the middle sector. The upper space of the upper cover is connected to the accommodating space of the lower base via the passage. The accommodating space of the lower base has a fluid communication with the exterior via the air outlet and the upper annular gap between the middle sector and the upper cover.

9 Claims, 8 Drawing Sheets

AIR PURIFIER

BACKGROUND OF THE INVENTION

1. Field of Invention

The invention relates to an air purifier and, in particular, to a machine that purifies air.

2. Related Art

FIG. 7 shows a conventional air purifier 8. An upper cover 82 is installed on the lower base 81. The lower base 81 is provided with a driving motor 83 to rotate the churning axle 84 and the blades 85 inside the lower base 81. As they rotate, air enters from the air intake 86 on the right-hand side of the upper cover 82 into the lower base 81. After mixing with a purifying fluid inside the lower base 81, the air is sent out via the air outlet 87 on the left hand side of the upper cover 82, thereby achieving the effect of purifying air.

FIG. 8 shows another conventional air purifier 9, whose structure is generally similar to the above mentioned air purifier 8 and includes a lower base 91, an upper cover 92, a driving motor 93, a churning axle 94, and blades 95. The left-hand side and right-hand side of the upper cover 92 in the drawing also have air intakes 96. The air outlet 97 of the air purifier 9 is downward on the right-hand side. It also achieves the effect of purifying air.

Although the above-mentioned conventional air purifiers 8, 9 have the function of purifying air, the exposed air intakes 86 and air outlets 87, 97 on the upper cover 82, 92 are indispensable structures of the conventional air purifiers. Even though such holes can be modified so that they are not too prominent, they cannot be completely hidden, posing a restriction in the design.

Besides, aside from the hardware design in appearance of the air purifiers 8, 9, there is no other structure to beautify their appearance. For example, the air purifiers 8, 9 do not have any light effect.

SUMMARY OF THE INVENTION

To solve the above-mentioned problems, an objective of the invention is to provide an air purifier with a revolutionary appearance design.

Another objective of the invention is to design the appearance so that it is more decorative.

To achieve the above-mentioned objectives, the disclosed air purifier includes:

a lower base having an accommodating space with an upward opening;

a middle sector disposed on the lower base, with a lower hemispherical part that is wider in the upper part and narrower in the lower part being exposed from the lower base, and the middle sector is surrounded by an annular shape that together with the upper rim of the lower hemispherical part form a lower annular gap;

an upper cover having an upper space disposed on the middle sector and exposing an upper hemispherical part with a wider lower part and a narrowed upper part, wherein the upper hemispherical part and the lower hemispherical part connect in the middle sector to form a spherical shape, and the middle sector with an annular surrounding together with the lower rim of the upper hemispherical part of the upper cover form an upper annular gap; and a blast component, a light-emitting element, a control unit, and a power supply base disposed in the middle sector between the lower base and the upper cover, with the blast component including a driving motor, a churning axle, and blades, the churning axle and the blades being located inside the accommodating space, the range of the light-emitting element covers the lower base, the middle sector, and the upper cover, and the power supplying providing the power required by the driving motor and the light-emitting element;

wherein the middle sector has a plurality of air intakes, a passage, and at least one air outlet hidden inside the upper cover, the upper space has a fluid communication with the exterior via the plurality of air intakes and the lower annular gap, and the upper space is connected with the accommodating space via the passage, and the accommodating space has a fluid communication with the exterior via the air outlet and the upper annular gap.

BRIEF DESCRIPTION OF THE DRAWINGS

These and other features, aspects and advantages of the invention will become apparent by reference to the following description and accompanying drawings which are given by way of illustration only, and thus are not limitative of the invention, and wherein.

DETAILED DESCRIPTION OF THE INVENTION

Figure 1:
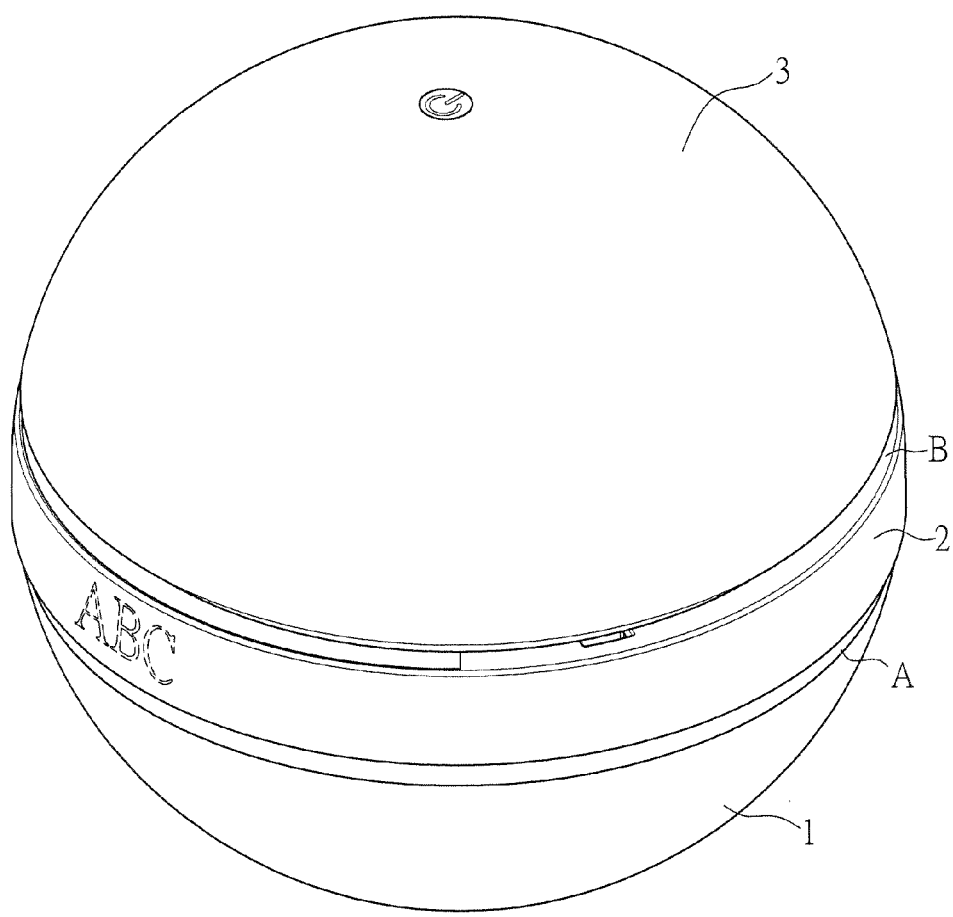
FIG. 1 is a three-dimensional perspective of the invention.

The present invention will be apparent from the following detailed description, which proceeds with reference to the accompanying drawings, wherein the same references relate to the same elements.

Please refer to FIGS. 1 to 6 for an embodiment of the invention. The embodiment shown in the drawings is only for illustration purpose, and should not be used to restrict the scope of the invention.

According to an embodiment of the invention, the invention is an air purifier comprising: a lower base 1, a middle sector 2, an upper cover 3, a blast component 4, a light-emitting element 5, a control unit 6, and a power supply base 7.

Figure 2:
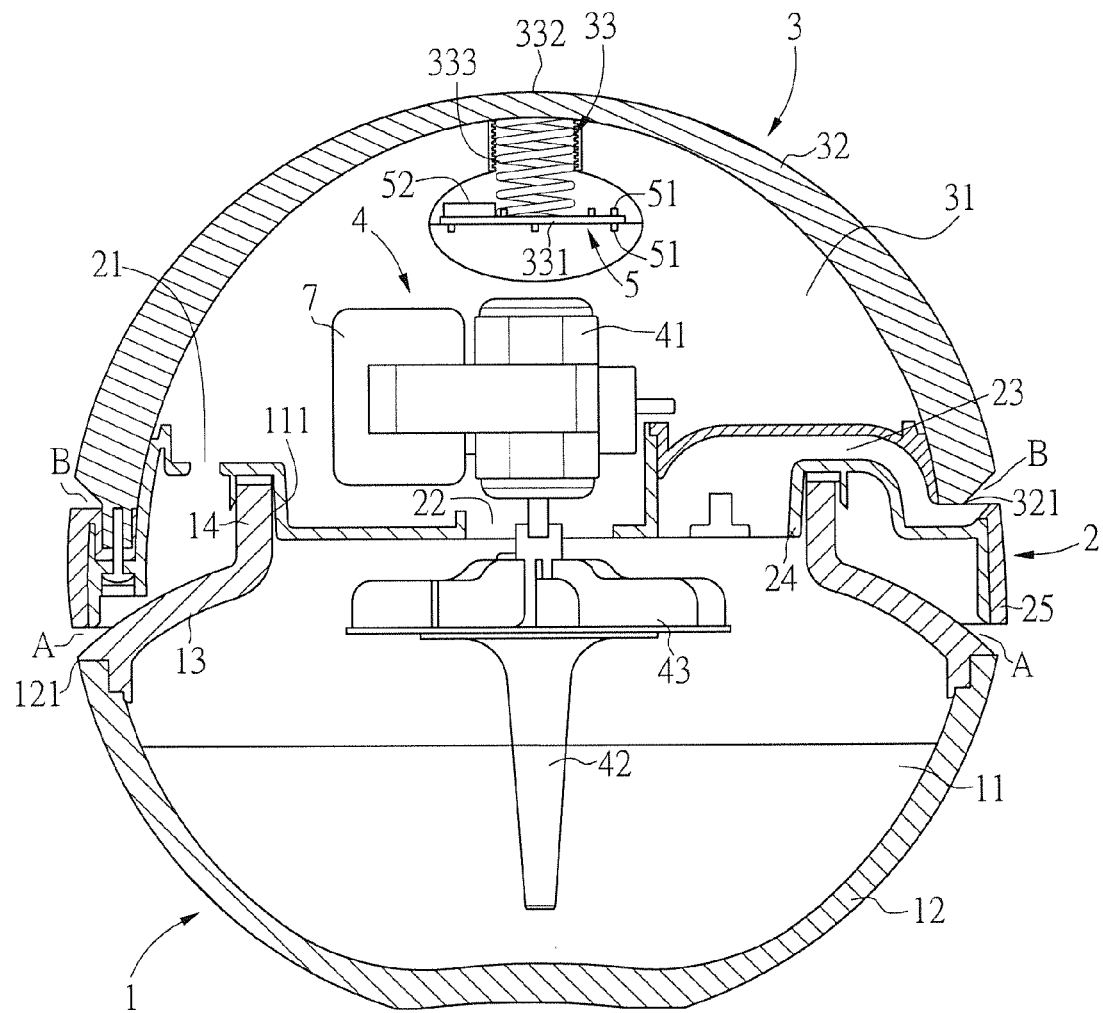
FIG. 2 is a cross-sectional view of the invention.

As shown in FIG. 2, the lower base 1 has an accommodating space 11 with an opening 111 upward. The middle sector 2 is disposed on the lower base 1. A lower hemispherical part 12 with a wider upper part and a narrower lower part is exposed from the lower base 1 when the middle sector 2 is disposed on the lower base 1. The middle sector 2 is surrounded by an annular shape, which together with the upper rim 121 of the lower hemispherical part 12 of the lower base 1 form the lower annular gap A.

As shown in FIG. 2, the upper cover 3 has an upper space 31. The upper cover 3 is disposed on the middle sector 2, exposing an upper hemispherical part 32 with a wider lower part and a narrower upper part. The upper hemispherical part 32 and the lower hemispherical part 12 are connected to form a sphere at the middle sector 2. An upper annular gap B is formed between the middle sector 2 with an annular surrounding and the lower rim 321 of the upper hemispherical part 32 of the upper cover 3.

Figure 3:
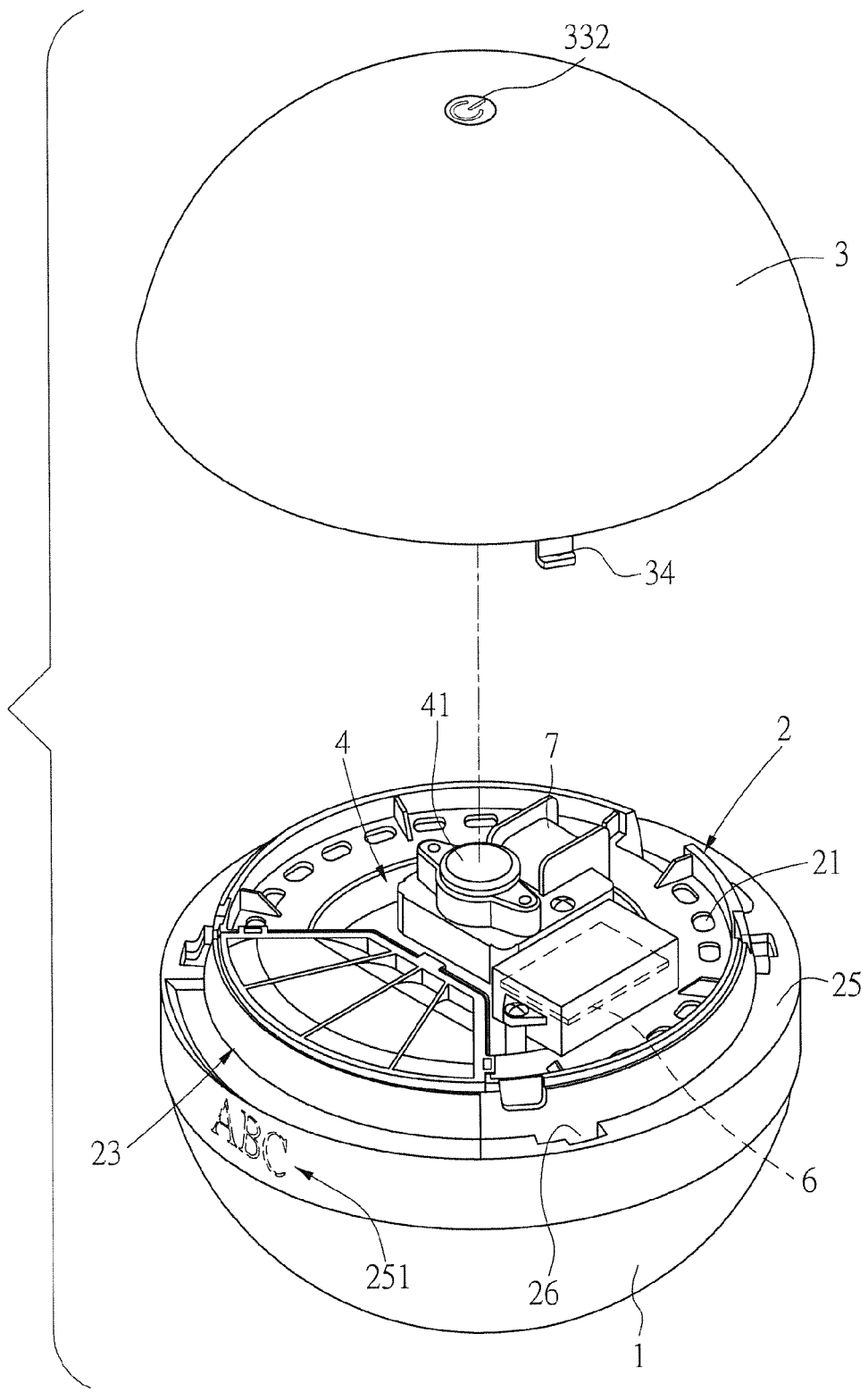
FIG. 3 is a exploded view of the invention when the upper cover is taken off the middle sector.

As shown in FIGS. 2 and 3, a blast component 4, a light-emitting element 5, a control unit 6, and a power supply base 7 are provided in the middle sector 2 between the lower base 1 and the upper cover 3. The blast component 4 includes a driving motor 41, a churning axle 42, and blades 43. The churning axle 42 and the blades 43 are in the accommodating space 11. The light-illuminating range of the light-emitting element 5 cover the lower base 1, the middle sector 2, and the upper cover 3. The power supply base 7 provides the electrical power required by the driving motor 41 and the light-emitting element 5.

Figure 4:
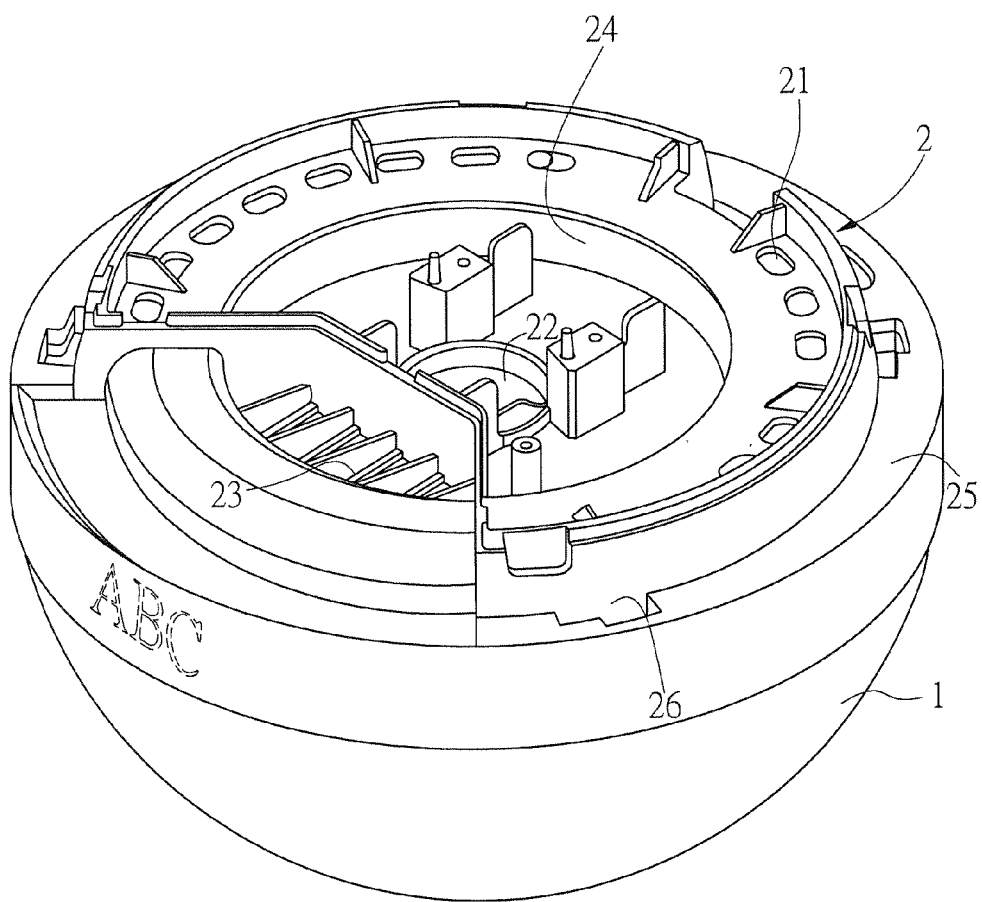
FIG. 4 is a structural view of the air intakes, passage, and air outlet of the middle sector according to the invention.
Figure 5:
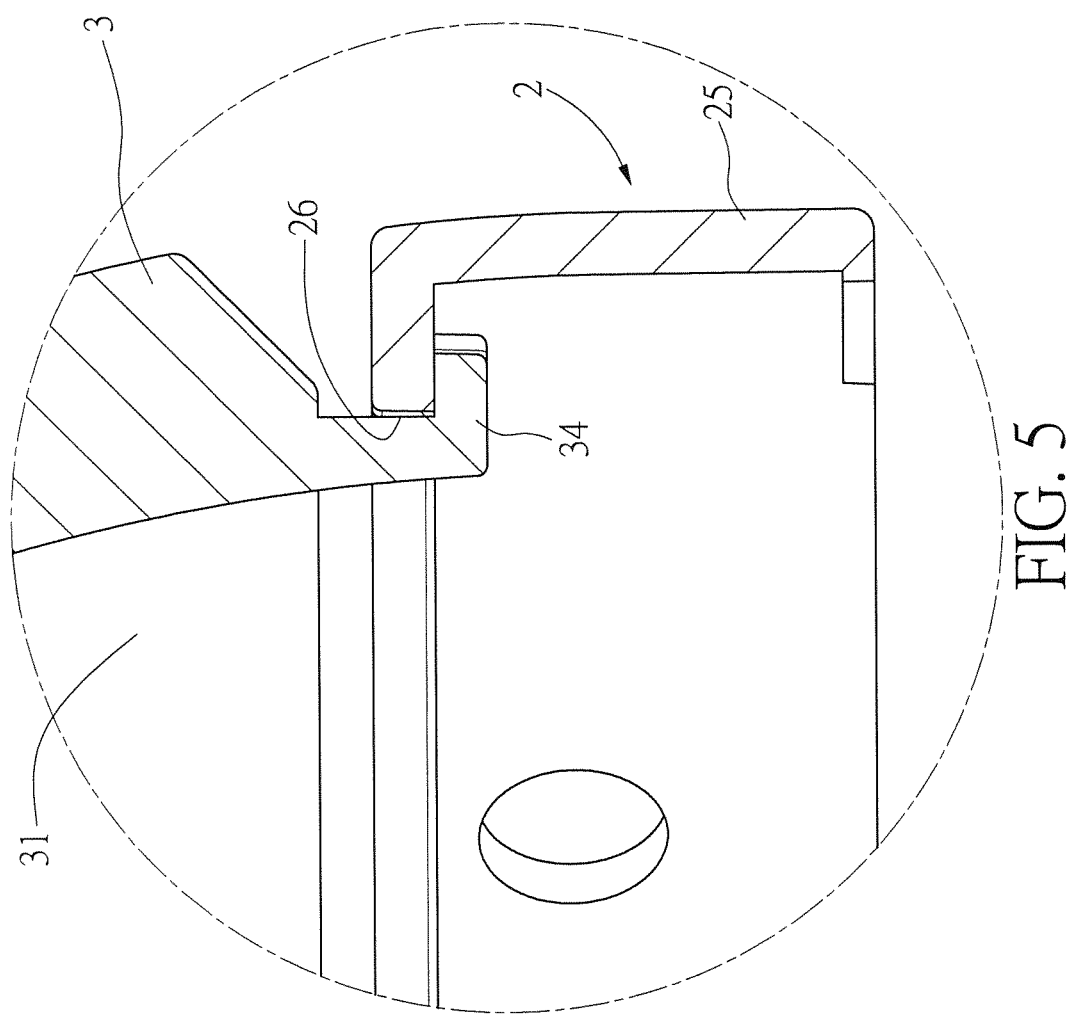
FIG. 5 is a locally enlarged view showing that the engaging parts of the upper cover engage the grooves of the middle sector.

As shown in FIGS. 2 and 4, the middle sector 2 has a plurality of air intakes 21, a passage 22, and an air outlet 23 hidden inside the upper cover 3. The upper space 31 has a fluid communication with the exterior via the plurality of air intakes 21 and the lower annular gap A. The upper space 31 and the accommodating space 11 are connected by the passage 22. The accommodating space 11 has a fluid communication with the exterior via the air outlet 23 and the upper annular gap B. In this embodiment, the passage 22 of the middle sector 2 is provided around the churning axle 42.

As shown in FIG. 2, the upper cover 3 has a switch 33 that includes a capacitive touch circuit board 331, a touching part 332, and a conductor 333. The capacitive touch circuit board 331 electrically connects to the control unit 6. The touching part 332 is displayed on the upper hemispherical part 32 formed from the outer shell. The conductor 333 is interposed between the capacitive touch circuit board 331 and the touching part 332. As one touches the touching part 332, the capacitive touch circuit board 331 is triggered by the conductor 333, thereby sending an ON or OFF signal to the control unit 6.

As shown in FIG. 2, the light-emitting element 5 includes a plurality of light-emitting diodes (LED's) 51 that can change color and a control chip 52. The control chip 52 is installed on the capacitive touch circuit board 331. The LED's 51 are distributed above and below the capacitive touch circuit board 331 and electrically connected to the control chip 52. The LED's 51 above the capacitive touch circuit board 331 illuminate the upper cover 3, while the LED's 51 below the capacitive touch circuit board 331 illuminate the middle sector 2 and the lower base 1. The control circuit 52 controls the colors of the LED's 51.

As shown in FIG. 2, the lower base 1 has a shrinking part 13 extended upward from the upper rim 121 of the lower hemispherical part 12. The top of the shrinking part 13 has a neck part 14 that forms the opening 111. The middle sector 2 has a ring part 24 that is aligned with the opening 111 and concave. The middle sector 2 is temporarily positioned on the neck part 14 as the ring part 24 is inserted into the opening 111. The middle sector 2 departs from the neck part 14 as one takes the ring part 24 away from the opening 111.

In this embodiment, the middle sector 2 is surrounded with an exposed outer ring frame 25. The outer ring frame 25 in this embodiment is pervious to light. Moreover, the outer ring frame 25 has a display part 251 that is more pervious to light than the outer ring frame 25. The display part 251 in this embodiment contains purely text. In other embodiments, the display part 251 may contain purely patterns or a combination of text and patterns.

In this embodiment, the middle sector 2 has a plurality of grooves 26 around it. The bottom rim of the upper cover 3 has engaging parts 34 corresponding to the grooves 26. The upper cover 3 is rotated to be positioned after the engaging parts 34 thereof are embedded into the grooves 26 around the middle sector 2.

When the disclosed air purifier is in use, one first take the middle sector 2 away from the lower base 1. After filling a purifying liquid in the accommodating space 11, the middle sector 2 is put back. Afterwards, the user uses his finger to touch the touching part 332 to start the air purifier. A signal is sent via the control unit 6 to start the driving motor 41. The churning axle 42 and the blades 43 are driven by the driving motor 41 to circulate air inside the air purifier.

Figure 6:
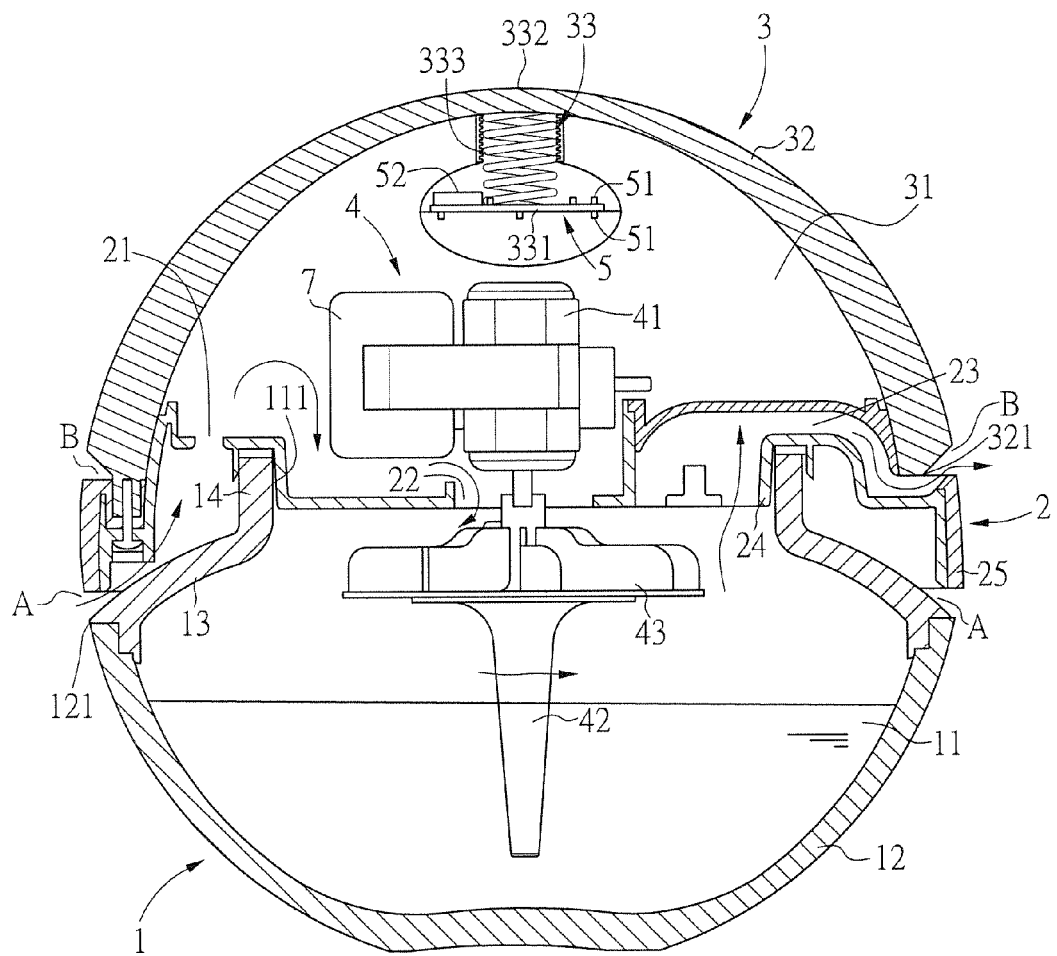
FIG. 6 is a schematic view of the invention in use.
Figure 7:
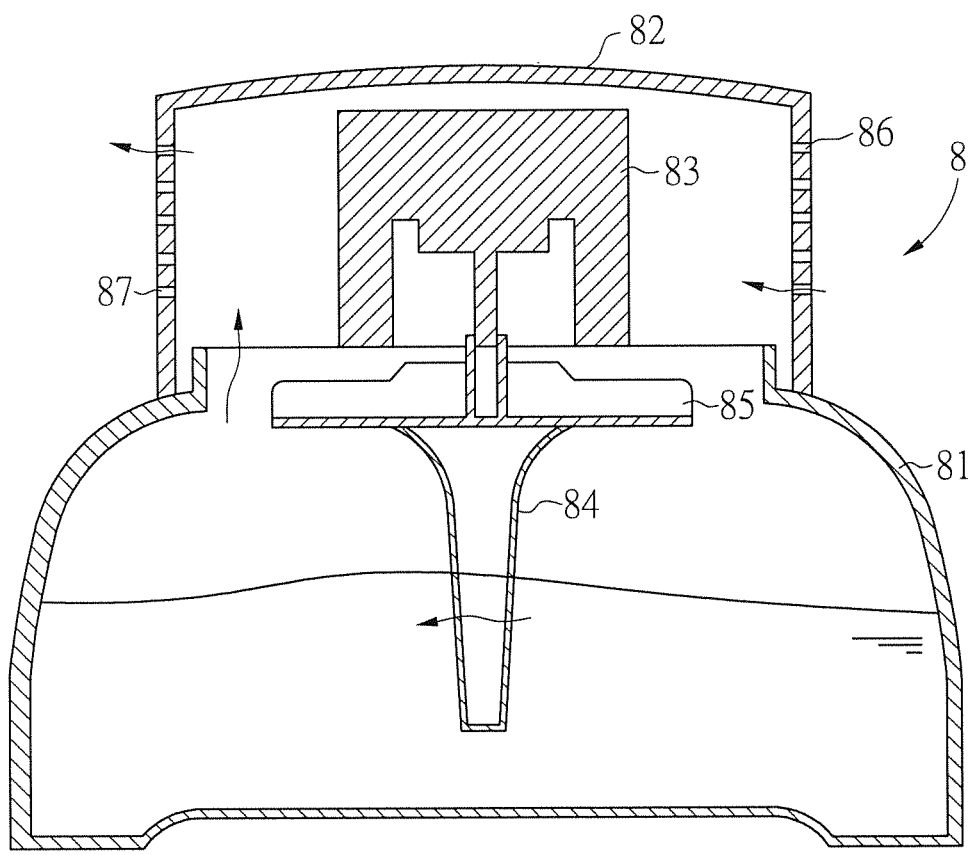
FIG. 7 is a cross-sectional view of a conventional air purifier.
Figure 8:
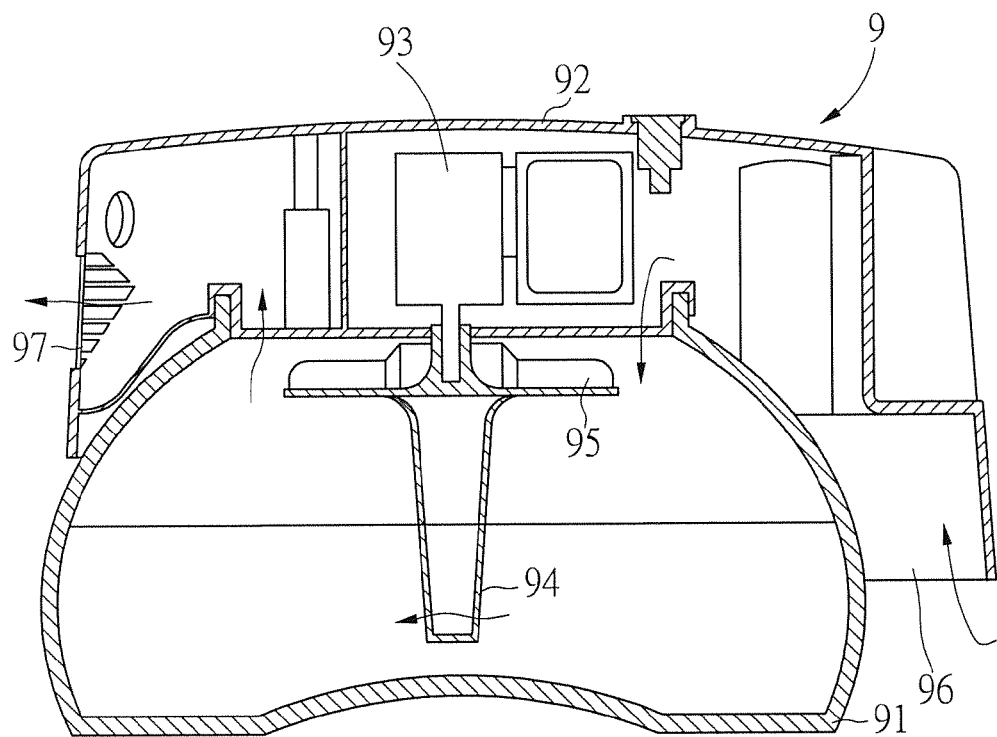
FIG. 8 is a cross-sectional view of another conventional air purifier.

As shown in FIG. 6, air circulates inside the air purifier because the blades 43 are rotated by the driving motor 41 to generate airflow. Exterior air enters via the lower annular gap A, and glows into the upper space 31 through the air intakes 21. Afterwards, the air flows from the upper space 31 to the accommodating space 11 via the passage 22. After the air and the purifying liquid get mixed there, the air flows to the air outlet 23 and, following the direction of the air outlet 23, to the upper annular gap B. The air then flows out of the upper annular gap B. The air is thus purified.

When the user's finger touches the touching part 332, a signal is sent via the control unit 6 to start the light-emitting element 5. Through the control of the control circuit 52, the LED's 51 above and below the capacitive touch circuit board 331 illuminate light and change colors. The illuminated light goes out through the upper cover 3 and the outer ring frame 25, particularly the display part 251 thereof.

From the above description, it is easier to see that the invention has the following advantages:

1. In view of the structure of the lower base 1, the middle sector 2, and the upper cover 3, the air intakes 21 and the air outlet 23 for air circulation are hidden. One only sees the sphere composed of the upper hemispherical part 32 and the lower hemispherical part 12, the upper annular gap B between the upper hemispherical part 32 and the middle sector 2, and the lower annular gap A between the lower hemispherical part 12 and the middle sector 2. Therefore, there is no need to worry about the exposed air intakes 21 and air outlet 23 in the appearance of the air purifier. The design in the appearance of the air purified thus has a breakthrough and is not restricted as in the prior art.

2. The light-emitting element 5 has a plurality of light-changing LED's 51. The control chip 52 controls to change the color of the light emitted by the LED's 51. During the process of purifying air, the air purifier also changes the color of its light. This renders the air purifier more decorative.

Although the invention has been described with reference to specific embodiments, this description is not meant to be construed in a limiting sense. Various modifications of the disclosed embodiments, as well as alternative embodiments, will be apparent to people skilled in the art. Therefore, it is contemplated that the appended claims will cover all modifications that fall within the true scope of the invention.

The invention claimed is:

1. An air purifier, comprising:
a lower base having an accommodating space with an upward opening;
a middle sector disposed on the lower base, with a lower hemispherical part that has a wider upper part and a narrower lower part being exposed from the lower base, and a lower annular gap formed between the annular surrounding of the middle sector and the upper rim of the lower hemispherical part of the lower base;
an upper cover having an upper space and disposed on the middle sector, with an upper hemispherical part that has a wider lower part and a narrower upper part being exposed from the upper cover, the upper hemispherical part and the lower hemispherical part being connected at the middle sector to form a sphere, and an upper annular gap formed between the annular surrounding of the middle sector and the lower rim of the upper hemispherical part;

a blast component, a light-emitting element, a control unit, and a power supply base disposed in the middle sector between the lower base and the upper cover, with the blast component including a driving motor, a churning axle and blades; the churning axle and the blades being inside the accommodating space; the illumination range of the light-emitting element covering the lower base, the middle sector, and the upper cover; and the power supply base providing the electrical power required by the driving motor and the light-emitting element;

wherein the middle sector has a plurality of air intakes, a passage, and at least one air outlet hidden inside the upper cover; the upper space has a fluid communication with the exterior via the air intakes and the lower annular gap; the upper space and the accommodating space are connected via the passage; and the accommodating space has a fluid communication with the exterior via the air outlet and the upper annular gap.

2. The air purifier of claim 1, wherein the upper cover has a switch that includes a capacitive touch circuit board electrically connected to the control unit, a touching part exposed to the exterior, and a conductor interposed between the capacitive touch circuit board and the touching part; an ON or OFF signal is transmitted to the control unit as a user touches the touching part to trigger the capacitive touch circuit board via the conductor.

3. The air purifier of claim 2, wherein the light-emitting element includes a plurality of light-emitting diodes (LED's) that has variable colors and a control chip; the control chip is installed on the capacitive touch circuit board and the LED's are distributed above and below the capacitive touch circuit board and electrically connected with the control chip; the LED's above the capacitive touch circuit board illuminate the upper cover, and the LED's below the capacitive touch circuit board illuminate the middle sector and the lower base; and the control chip controls the color of light emitted from the LED's.

4. The air purifier of claim 1, wherein the lower base has a shrinking part extended from the upper rim of the lower hemispherical part, and the top of the shrinking part has a neck part to form the opening; the middle sector has a ring part that is aligned with the opening and concave; the middle sector is temporarily positioned on the neck part as the ring part is inserted into the opening, and the middle sector departs from the neck part when the ring part is taken away from the opening.

5. The air purifier of claim 1, wherein the passage of the middle sector is provided around the churning axle.

6. The air purifier of claim 1, wherein the lower base, the middle sector, and the upper cover are pervious to light, and one thereof contains the display part that is more pervious to light.

7. The air purifier of claim 6, wherein the display part contains text, patterns, or a combination thereof.

8. The air purifier of claim 7, wherein the middle sector is surrounded with an exposed outer ring frame, and the display part is on the outer ring frame.

9. The air purifier of claim 1, wherein the middle sector is surrounded with a plurality of grooves, the bottom rim of the upper cover has an engaging part corresponding to each of the grooves, and the upper cover is rotated to be positioned as the engaging parts are embedded into the grooves around the middle sector.

* * * * *